United States Patent
Sharma

(10) Patent No.: US 12,427,267 B1
(45) Date of Patent: Sep. 30, 2025

(54) INJECTOR DEVICE

(71) Applicant: Sunil Sharma, Jacksonville, FL (US)

(72) Inventor: Sunil Sharma, Jacksonville, FL (US)

( * ) Notice: Subject to any disclaimer, the term of this patent is extended or adjusted under 35 U.S.C. 154(b) by 0 days.

(21) Appl. No.: 19/041,939

(22) Filed: Jan. 30, 2025

(51) Int. Cl.
- *A61M 5/32* (2006.01)
- *A61M 5/20* (2006.01)
- *A61M 5/31* (2006.01)
- *A61M 5/34* (2006.01)

(52) U.S. Cl.
CPC ............ *A61M 5/3234* (2013.01); *A61M 5/20* (2013.01); *A61M 5/3148* (2013.01); *A61M 5/34* (2013.01); *A61M 2005/2013* (2013.01)

(58) Field of Classification Search
CPC .... A61M 5/3234; A61M 5/20; A61M 5/3137; A61M 5/32; A61M 5/3287; A61M 5/1452; A61M 5/3148; A61M 5/422; A61M 5/34; A61M 2005/2013; A61M 2005/341; A61M 16/104; A61B 2017/00238
See application file for complete search history.

(56) References Cited

U.S. PATENT DOCUMENTS

| | | | | |
|---|---|---|---|---|
| 1,503,399 A | * | 7/1924 | Webb | A61M 5/32 604/273 |
| 2005/0137575 A1 | * | 6/2005 | Thompson | A61M 5/31581 600/114 |
| 2007/0265573 A1 | * | 11/2007 | Fojtik | A61B 5/150259 604/187 |

OTHER PUBLICATIONS

Schumann, R. (2011). Anaesthesia for bariatric surgery. Best Practice & Research Clinical Anaesthesiology, 25(1), 83â93. https://doi.org/10.1016/j.bpa.2010.12.006 (Year: 2011).*

* cited by examiner

*Primary Examiner* — Tasnim Mehjabin Ahmed
(74) *Attorney, Agent, or Firm* — Camille A. Wilson; Wilson Dutra, PLLC

(57) ABSTRACT

An injector device may include an injector handle with a compression mechanism configured to create pressure between the injector handle. Applying pressure to the injector handle may release fluids contained within a fluid containing portion. A loading mechanism may be configured to slide, wherein the loading mechanism may be configured to create a suction force to draw fluids into the fluid containing portion. A first locking mechanism may be positioned between the fluid containing portion and the canula, wherein the first locking mechanism may connect the fluid containing portion to the canula. A second locking mechanism may be positioned between the canula and a needle, wherein the second locking mechanism may connect the canula to the needle, wherein the canula and the needle may include an internal cavity connected the fluid containing portion, wherein the fluids are configured to enter and exit at the needle.

17 Claims, 10 Drawing Sheets

INJECTOR DEVICE

BACKGROUND

Injection devices are popular tools for administering medications like insulin, vaccinations, and numbing agents. Conventional syringes equipped with needles are usually sufficient for delivering injections to superficial anatomical sites. As surgical procedures have advanced, more sophisticated methods of medical injections have developed. For example, there are injectors that deliver medication to deeper targeted tissues and organs. In orthopedic applications, such as joint therapy, an injector may directly target an anatomical structure with image guidance to administer a precise quantity of drug.

As the field of medicine continues to evolve, the demands for better injection techniques and devices follow. Over the years, surgery has advanced from open procedures, laparotomy, to minimally invasive procedures, laparoscopy, but the injection techniques and devices have not yet advanced to the same degree. There is a need for injection devices that are easier for a medical practitioner to handle while administering medications laparoscopically with precision. As it stands, injection devices require two hands or more for the medical practitioner to withdraw the necessary substance and to inject it into a patient. This limitation may hinder a medical practitioner's ability to stabilize, reposition, or adjust a patient during a procedure that may result in suboptimal results.

In addition to the reliability and ease of use, there is a demand for an injection device that may reach deeper tissues and internal organs with minimal risk to a patient. Current devices are mostly optimized for superficial or subcutaneous injections, which limits their use and applicability to internal structures. These existing devices are limited by structural integrity and precision of the injector devices. During laparoscopy small ports are inserted through the abdominal wall and the abdomen is inflated with air creating a space between the skin and internal structures. Due to this space, long, thin instruments are needed to reach the intra abdominal structures. There is currently no device long enough to directly inject under laparoscopic vision. When performing laparoscopic surgeries, certain groups of nerves, like the celiac plexus, are already visible and accessible. With an injector device capable of reaching the celiac plexus one may ease pain after surgeries targeting the abdominal region. Current procedures rely on external imaging techniques like a computed tomography (CT) scan or fluoroscopy which take days to provide results. There is an opportunity with laparoscopic surgeries to avoid these imaging techniques as medical practitioners have direct visualization of the celiac plexus region. The use of these techniques may also reduce the time spent in a medical facility after surgery as numbing this area directly may have the effect of significantly reducing symptoms associated with these types of surgeries like vomiting, pain, and nausea.

What is needed is a tool or method of injection that overcomes these deficiencies. If an injector device was capable of quickly withdrawing and precisely administering fluid to a patient without the need for imaging, this may allow injection techniques to evolve. A device that is safe and accurate for deep-tissue and internal organ delivery with these features may allow for new and helpful practices.

SUMMARY OF THE DISCLOSURE

What is needed is an injector device configured to withdraw and deposit fluids laparoscopically. In some aspects, the injector device may be capable of quickly withdrawing fluids and administering it to a patient through a port in the abdominal wall with minimal effort.

In some embodiments, the injector device may include a fluid containing portion that may include a fluid transfer end and a fluid control end distally located from the fluid transfer end, wherein the fluid containing portion may be configured to contain a predetermined amount of fluid, wherein the fluid may be received and ejected through the fluid transfer end, and wherein the fluid control end may be configured to connect the fluid containing portion to a loading mechanism. In some aspects, the injector device may include an injector handle with a compression mechanism that may be configured to create pressure between the injector handle, wherein applying pressure to the injector handle may be configured to release a predetermined amount of fluid contained in the fluid containing portion through the fluid transfer end.

In some implementations, the injector device may include the loading mechanism detachably connected to the fluid control end and above the injector handle that may be configured to slide within the fluid containing portion positioned adjacent to the loading mechanism, wherein the loading mechanism may be configured to draw in a predefined amount of fluid into the fluid containing portion. In some embodiments, the injector device may include a canula that may include rigid body with a first end and a second end distally located from the first end, wherein the rigid body may include a cylindrical extension, wherein the second end may be detachably connected to the fluid dispensing end.

In some embodiments, the injector device may include a needle that may include an attaching end and an injecting end, wherein the attaching end may be detachably connected to the first end of the canula. In some aspects, the injector device may include a first locking mechanism that may be detachably connected to the fluid transfer end of the fluid containing portion to the second end of the of the canula. In some implementations, the injector device may include a second locking mechanism configured to detachably connect the first end of the canula to the attaching end of the needle, wherein the needle and the canula may include an internal cavity connectable to the fluid containing portion, wherein the fluid may be configured to enter and exit at the needle.

A number of embodiments of the present disclosure will be described. While this specification contains many specific implementation details, these should not be construed as limitations on the scope of any disclosures or of what may be claimed, but rather as descriptions of features specific to particular embodiments of the present disclosure. It is understood to those skilled in the art that variations, modifications, and alterations may be apparent. It will be understood that various modifications may be made without departing from the spirit and scope of the disclosure.

BRIEF DESCRIPTION OF THE DRAWINGS

The accompanying drawings that are incorporated in and constitute a part of this specification illustrate several embodiments of the disclosure and, together with the description, serve to explain the principles of the disclosure.

DETAILED DESCRIPTION

Figure 1:
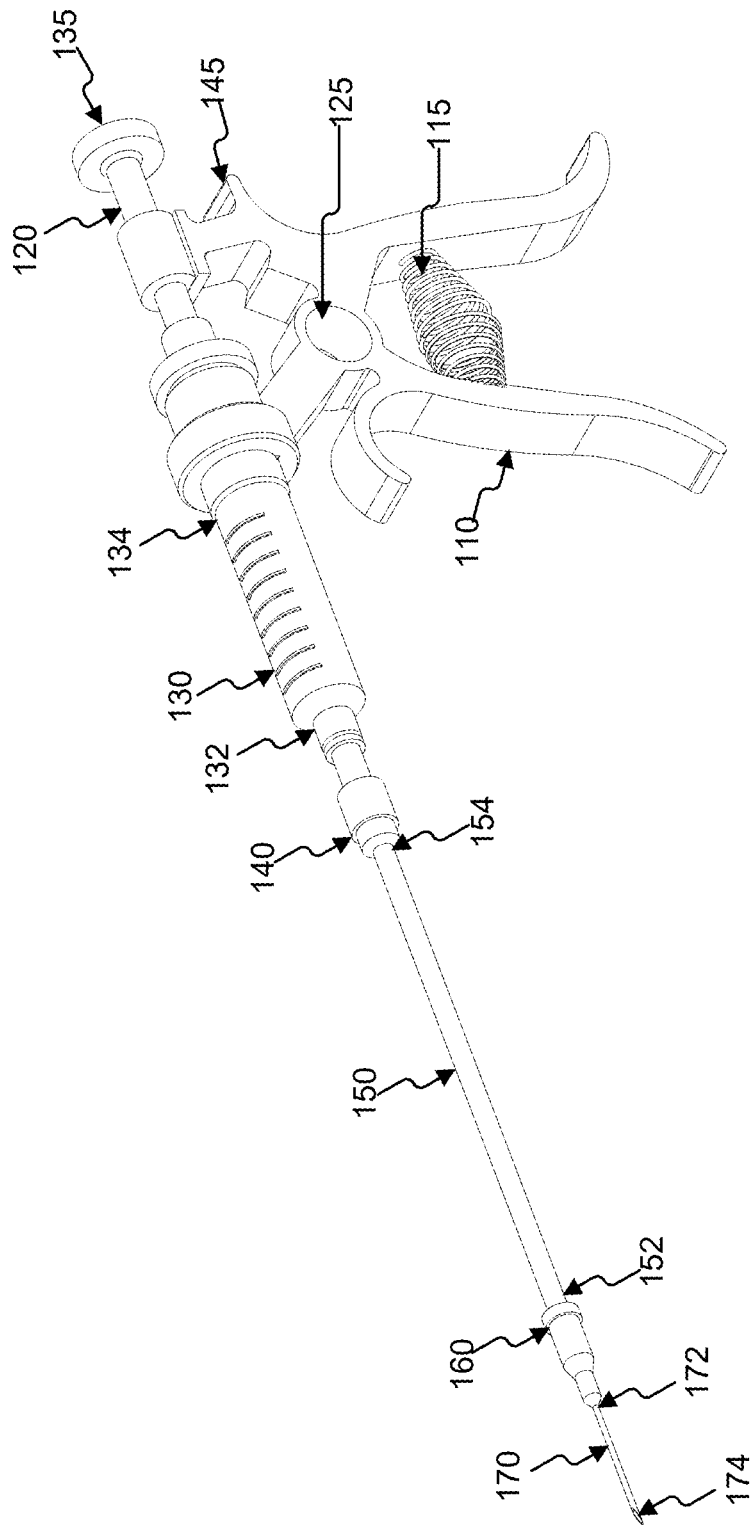
FIG. 1 illustrates an injector device according to some embodiments of the present disclosure.

The present disclosure provides generally for an injector device configured to withdraw and deposit fluids. According to the present disclosure, the injector device may include an injector handle, a loading mechanism, a first locking mechanism, a fluid containing portion, a second locking mechanism, and a needle.

In the following sections, detailed descriptions of examples and methods of the disclosure will be given. The description of both preferred and alternative examples, though thorough, are exemplary only, and it is understood to those skilled in the art that variations, modifications, and alterations may be apparent. It is therefore to be understood that the examples do not limit the broadness of the aspects of the underlying disclosure as defined by the claims.

Glossary

Injector device: as used herein refers to a device configured to administer fluids. In some aspects, the injector device may include an injector handle, a loading mechanism, a fluid containing portion, a canula, a first locking mechanism, a second locking mechanism, and a needle. In some embodiments, the injector device may provide the controlled suction and injection of fluids. In some aspects, the fluids may include prescription drugs and numbing agents.

Fluid containing portion: as used herein refers to a portion of the injection device configured to receive and contain the fluids received by the injection device.

Loading Mechanism: as used herein refers to the mechanism configured to slide in and out of the fluid containing portion, wherein the movement of the loading mechanism may create a suction force that may draw fluids in or may create an expelling force that may force fluids out of the injector device.

Injector handle: as used herein refers to the handle of the injector device, wherein the injector handle may be gripped by a user. In some aspects, the injector handle may include a compression mechanism, wherein pressure may be applied to the injection handle to push fluids out of the injector device.

Compression device: as used herein refers to a feature of the injector handle configured to create pressure when force may be applied to the injector handle. In some aspects, the compression device may be configured to ensure controlled and precise ejections of fluids from the injector device.

Locking mechanism: as used herein refers to feature of the loading mechanism that may be configured to prevent the fluids from exiting the injector device, wherein the locking mechanism may be configured to lock the loading mechanism in its place. In some aspects, applying force to the injector handle may be configured to release the locking mechanism in a controller manner.

Celiac plexus: as used herein refers to a network of nerves located in the abdomen near the celiac artery. In some embodiments, providing anesthetic to the celiac plexus may reduce pain in the abdominal region.

Laparoscopic surgery: as used herein refers to a minimally invasive surgical technique wherein small incisions may be made and instruments may be inserted through ports to perform procedures while a surgeon views the anatomy on a imaging screen.

Veress Needle: as used herein refers to a long needle commonly used in laparoscopic surgery to access and inflate the abdomen with air to create a working space for a medical practitioner.

Pneumoperitoneum: as used herein refers to the process of using the Veress needle with air or gas during laparoscopic surgery to create a clear view and working space for the medical practitioner.

Referring now to FIG. 1, an injector device according to some embodiments of the present disclosure, is illustrated. In some embodiments, the injector device may include an injector handle 110, a loading mechanism 120, a fluid containing portion 130, a first locking mechanism 140, a canula 150, a second locking mechanism 160, and a needle 170. In some embodiments, the injector device may include an injector handle 110. In some aspects, the injector handle 110 may be contoured for ergonomic engagement. In some implementations, the injector handle 110 may include a compression mechanism 115, wherein the compression mechanism 115 may create pressure between the injector handle 110. In some aspects, the compression mechanism 115 may include a spring, as a non-limiting example.

In some embodiments, the injector handle 110 may include at least one malleable mechanism 125, wherein the injector handle 110 may protrude from the at least one malleable mechanism 125, wherein the malleable mechanism 125 may be above the compression mechanism 115 and the injector handle 110 and below the fluid containing portion 130 and the loading mechanism 120. In some aspects, the at least one malleable mechanism 125 may be configured to allow movement of the injector handle 110, wherein the at least one malleable mechanism 125 may be configured to bend when pressure may be applied to the injector handle 110. In some implementations, the injector device may include a loading mechanism 120, wherein the loading mechanism 120 may be configured to slide in and out of the fluid containing portion 130.

In some aspects, the loading mechanism 120 may include a knob 135 at its end, wherein the knob 135 may be configured to provide leverage to pull the loading mechanism 120. In some implementations, the pulling of the loading mechanism 120 may create a suction force, wherein the suction force may draw fluids into the fluid containing portion 130. In some aspects, the knob 135 may be configured as a stopper, wherein the knob 135 may prevent the loading mechanism 120 from exiting the injector device.

In some embodiments, the loading mechanism 120 may include a stopping mechanism 145, wherein the stopping mechanism 145 may prevent the dispensing of any fluids held in the fluid containing portion 130 unless pressure may be applied to the injector handle 110. In some aspects, the stopping mechanism 145 may include be configured to be pressed down, wherein the stopping mechanism 145 prevents the loading mechanism 120 from being moved. In some implementations, the stopping mechanism 145 may be configured to prevent the loading mechanism 120 from moving once the fluid containing portion 130 may be filled with fluid, wherein applying pressure to the injector handle 110 may be configured disable the stopping mechanism 145 to enable the injector device to expel the fluid from the fluid containing portion 130. In some aspects, the stopping mechanism 145 may include a tab that may be pressed down, wherein the pressing down of the tab activates the locking mechanism 145.

By way of example and not limitation, the loading mechanism 120 may be pulled to draw fluids into the fluid containing portion 130, wherein the squeezing of the injector handle 110 may be configured to slowly release the loading mechanism 120 to dispense the fluids. In some aspects, the release of the fluids in the fluid containing portion 130 may be correlated to the amount of pressure applied to the injector handle 110. In some implementations, a spring may be located on the loading mechanism 120 to create a pressure to allow for more controlled withdrawal of fluids.

In some embodiments, the fluid containing portion 130 may be configured to contain fluids, wherein the fluid containing portion 130 may receive the fluids suctioned by the loading mechanism 120. In some implementations, the fluid containing portion 130 may include a fluid transfer end 132 and a fluid control end 134 distally located from the fluid transfer end 132, wherein the fluid containing portion 130 may be configured to contain a predetermined amount of fluid, wherein the fluid may be received and ejected through the fluid transfer end 132. In some aspects, the fluid control end 134 may be configured to connect to a loading mechanism 120, wherein the loading mechanism 120 may be detachably connected to the fluid control end 132 and above the injector handle 110 configured to slide within the fluid containing portion 130 positioned adjacent to the loading mechanism 120.

In some implementations, the canula 150 may include a rigid body with a first end 152 and a second end 154 distally located from the first end 152. In some aspects, the rigid body may include a cylindrical extension, wherein the second end 154 may be detachably connected to the fluid dispensing end 132. In some aspects, fluid containing portion 130 may connect to a canula 150 using a first locking mechanism 140. In some aspects, the first locking mechanism 140 may be connectable to the fluid containing portion 130, wherein the first locking mechanism 140 may be configured to connect the fluid containing portion 130 to the canula 150. In some embodiments, the canula 150 may include a rigid material configured to extend the distance of injector device.

In some implementations, the end of the canula 150 further opposite the fluid containing portion 130 may include a second locking mechanism 160, wherein the second locking mechanism 160 includes a male portion and a female portion. In some aspects, the female portion may be positioned on the needle 170, wherein the female portion may receive the male portion on the canula 150. In some aspects, the female portion of the second locking mechanism 160 may be configured to on the needle 170

In some embodiments, the needle 170 may include an attaching end 172 and an injecting end 174, wherein the attaching end 172 may be detachably connected to the first end 152 of the canula 150. In some aspects, the second locking mechanism 160 may be configured to detachably connect the first end 152 of the canula 150 to the attaching end 172 of the needle 170.

In some aspects, the second locking mechanism 160 may be configured as a Luer lock, wherein the second locking mechanism 160 may create a secure, leak-roof connection between the canula and the needle 170. By way of example and not limitation, the female portion may include a threaded interior configured to receive the male portion. By way of example and not limitation, the needle 170 already being on the engaging component may reduce the risk of needle breakage.

In some aspects, the male portion may lock into the female portion with minimal force, wherein a user may gently place the injector device onto the male portion to apply the needle 170 before use. In some implementations the canula 150 and the needle 170 may include an internal cavity, wherein a fluid may enter or exit the needle 170. In some aspects, the fluid may enter the needle 170 when the loading mechanism 120 may be pulled. In some aspects, the fluid may deposit the needle 170 when pressure may be applied to the injector handle 110.

By way of example and not limitation, the injector device may be utilized in a laparoscopic surgery to administer local anesthesia. In some aspects, a port may be positioned on the abdomen of a patient, as a non-limiting example, wherein the port may provide access to the patient's deep tissue and internal organs. By way of example and not limitation, the port may provide access directly to the celiac plexus, wherein the injector device may be positioned such that the canula 150 and the needle 170 may be inserted into the port. In some embodiments, the port may include a disc-like entryway, wherein the port may be a rigid structure with a circular aperture that may be placed on an opening of a patient's body to keep it open and visible. In some aspects, the needle may pierce the celiac ganglia to administer local anesthesia. By way of example and not limitation, the injection of local anesthesia to the celiac ganglia may eliminate or reduce pain during and after the laparoscopic surgery. In some aspects, the injector device may inject anesthesia to the celiac plexus during laparoscopic surgery to reduce symptoms of nausea, vomiting, and pain that may be typically associated with such surgeries. By way of example and not limitation, a patient may be able to walk and be discharged shortly after surgery, significantly reducing the amount of time spent recovering in a medical facility.

Figure 2:
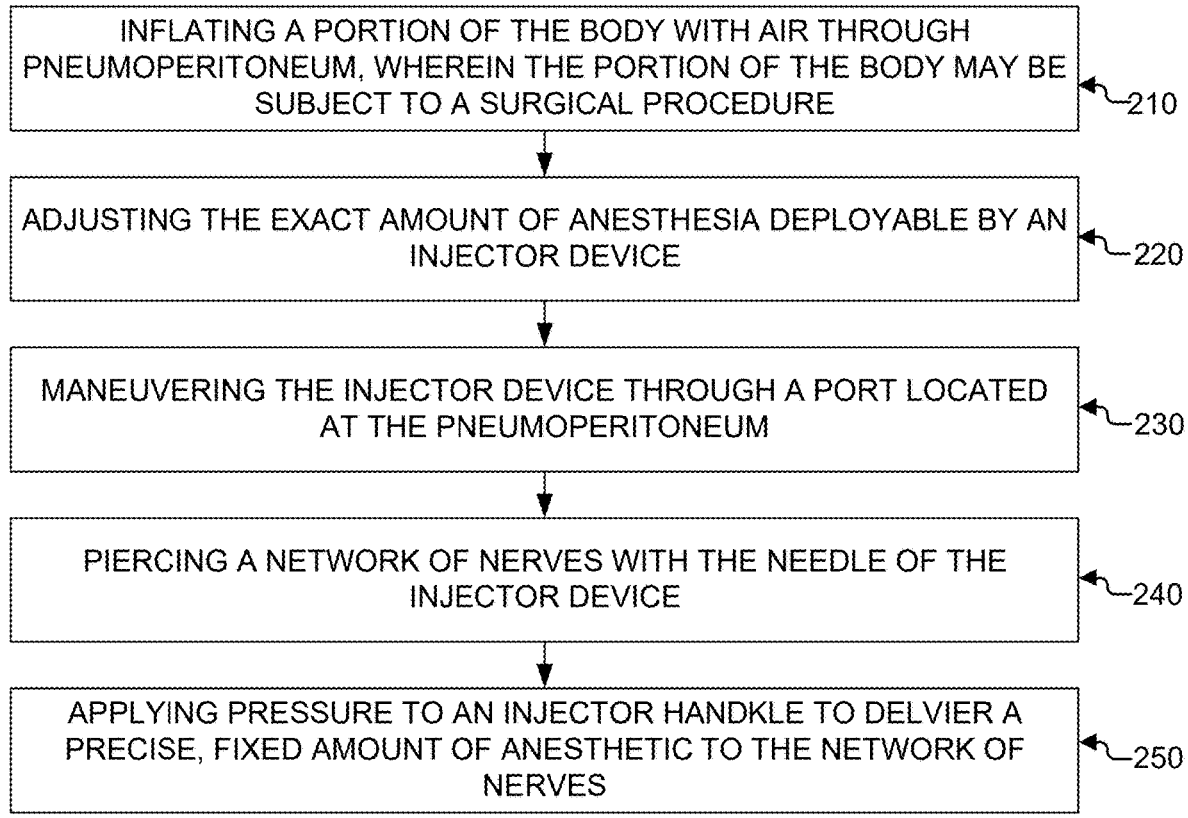
FIG. 2 illustrates a method of injecting anesthesia, according to some embodiments of the present disclosure.

Referring now to FIG. 2, a method of injecting anesthesia, according to some embodiments of the present disclosure, is illustrated. At 210, inflating a portion of the body with air through pneumoperitoneum, wherein the portion of the body may be subject to a surgical procedure. In some aspects, the surgical procedure may have been laparoscopic surgery. By way of example and not limitation, the air may inflate the abdomen with a Veress needle. At 220, adjusting the exact amount of anesthesia deployable by an injector device. In some embodiments, the injector device may include an adjustment mechanism configured to adjust the amount of anesthesia expelled by the injector device.

At 230, maneuvering the injector device through a port located at the pneumoperitoneum. In some aspects, the port may be configured to minimize air leakage while the injector device is being inserted or removed, wherein the port may provide an entry point for the injector device. In some aspects, the port may be placed on the body to provide direct access to deep tissue or internal organs, as non-limiting examples. At 240, piercing a network of nerves with the needle of the injector device. In some aspects, the length of a canula of the injector device may be configured to traverse through the pneumoperitoneum and may be directed under visualization of a medical practitioner through a laparoscope.

At 250, applying pressure to an injector handle to deliver a precise, fixed amount of anesthetic to the network of nerves. By way of example and not limitation, the network of nerves may be the celiac plexus, wherein the application of anesthesia may reduce abdominal pain following laparoscopic surgery. In some embodiments, the injector handle may be ergonomically configured, wherein the amount of pressure applied to the injector handle may determine the amount of anesthesia expelled from the needle. In some implementations, the injector device may include fluid containing portion, wherein the fluid containing portion may be configured to contain a predetermined amount of anesthesia. In some aspects, the predetermined amount of anesthesia may be forced out of the fluid containing portion through the canula and out of the needle in a controlled manner based on the pressure that may be applied to the injector handle.

In some implementations, the injector device may include a adjustment mechanism configured to adjust the exact amount of anesthesia. In some aspects, the method may further include replacing the needle with a new needle after the needle has been used. In some embodiments, the method may further include assembling the injector device prior to inflating the portion of the body with air through pneumoperitoneum, wherein the needle, the canula, the fluid containing portion, and the handle may be connectable through one or more locks configured to keep the device securely together.

Figure 3:
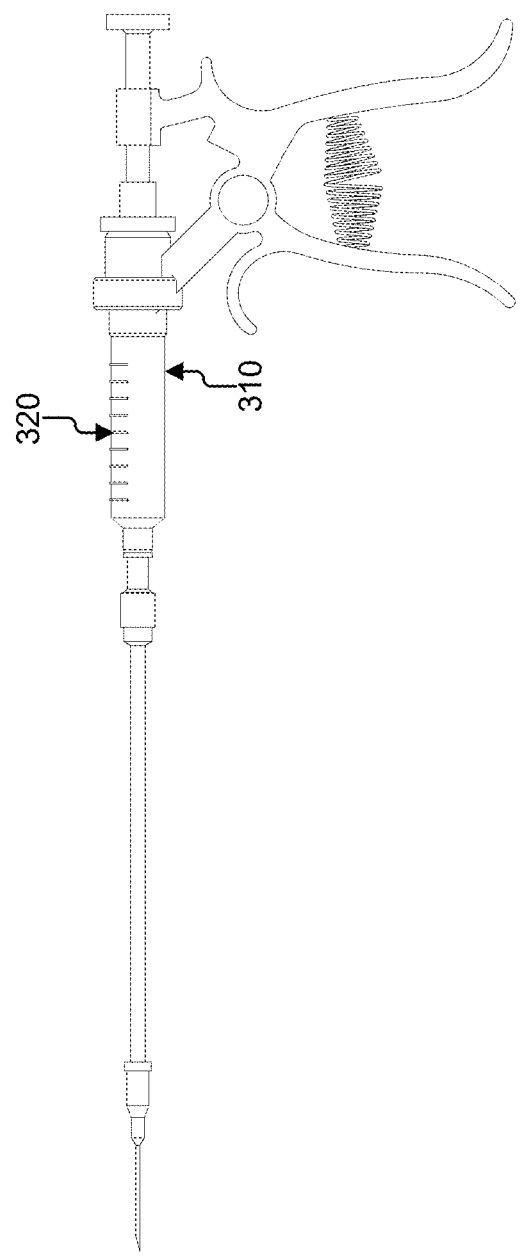
FIG. 3 illustrates an injector device according to some embodiments of the present disclosure.

Referring now to FIG. 3, an injector device according to some embodiments of the present disclosure, is illustrated. In some embodiments, the injector device may include a fluid containing portion 310. In some aspects, the fluid containing portion 310 may include one or more measurement marks 320 configured to measure any fluid that enters the fluid containing portion 310. In some aspects, the fluid may include anesthesia. In some implementations, the injector device may be configured to deliver a controlled, precise quantity of anesthesia to a targeted body portion. In some aspects, the targeted body portion may include a network of nerves, an organ, or tissue, as non-limiting examples.

Figure 4:
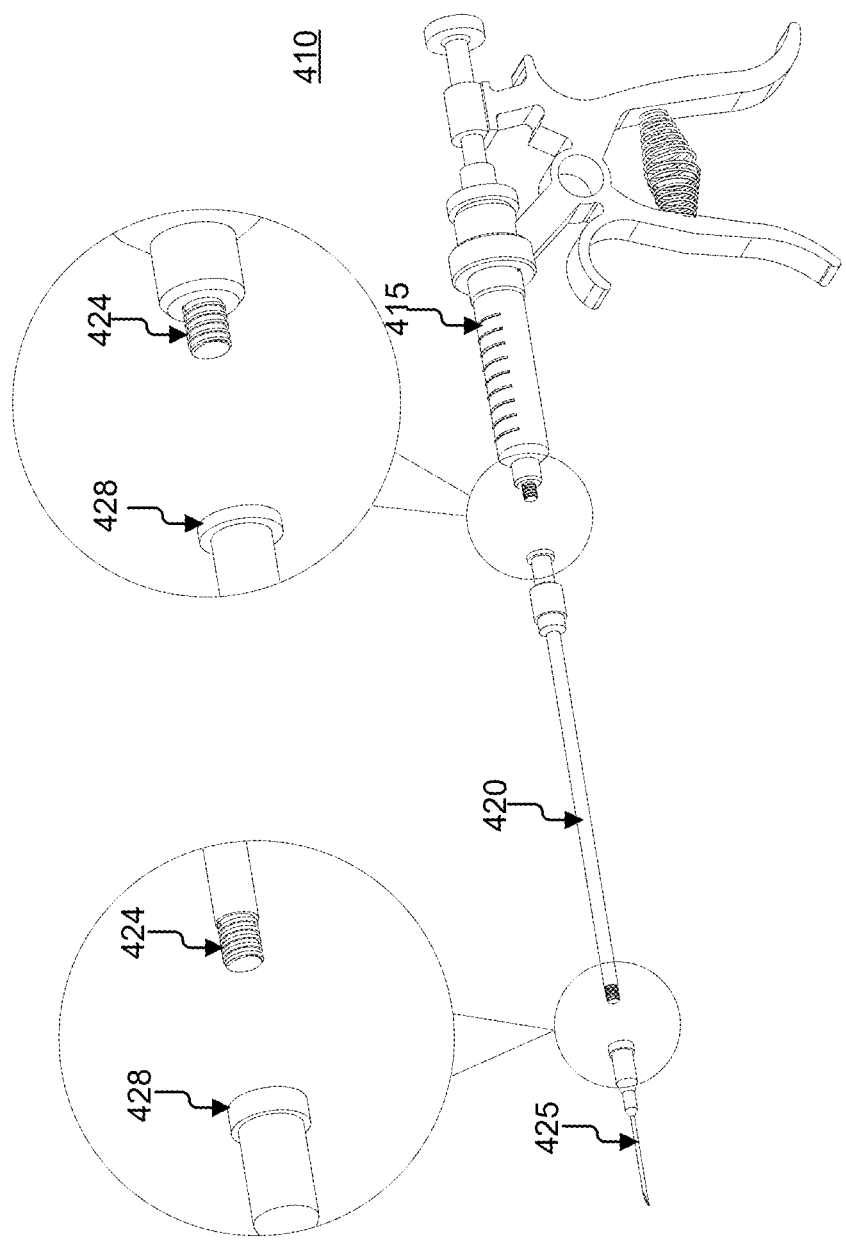
FIG. 4 illustrates an injector device, according to some embodiments of the present disclosure

Referring now to FIG. 4, an injector device, according to some embodiments of the present disclosure, is illustrated. In some embodiments, the injector device 410 may include a fluid containing portion 415, canula 420, and a needle 425. In some implementations, the canula 420 may include a male locking mechanism 424 and a female locking mechanism 428. In some aspects, the fluid containing portion 415 may include a male locking mechanism 424. In some aspects, the needle may include a female locking mechanism 428. By way of example and not limitation, the male locking mechanism 424 may include a protruding element configured to be received by the female locking mechanism 428.

In some aspects, the protruding element of the male locking mechanism 424 may include a threaded exterior, wherein a cavity of the female locking mechanism 428 may include a threaded interior configured to receive the male locking mechanism 424, as a non-limiting example. In some embodiments, the male locking mechanism 424 and the female locking mechanism 428 may be configured to connect the canula 420 to the fluid containing portion 415 and the needle 425 to the canula 420, wherein the fluid containing portion 415 may include the remaining portions of the injector device 410. In some implementations, the male locking mechanism 424 may include a Luer lock. In some aspects, the female locking mechanism 428 may include a Huber lock. In some embodiments, the fluid containing portion 415, the canula 420, and the needle 425 may include a partially hollow interior, wherein fluid may travel through the partially hollow interior and exit through the end of the needle 425.

Figure 5:
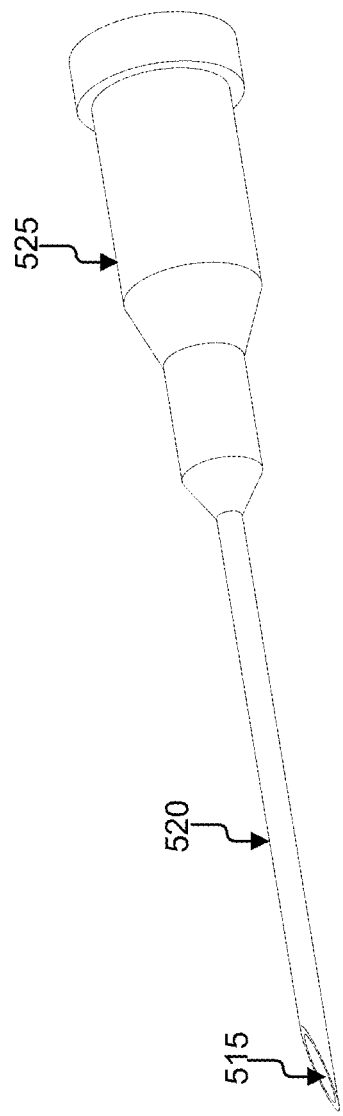
FIG. 5 illustrates a needle of an injector device, according to some embodiments of the present disclosure

Referring now to FIG. 5, a needle of an injector device, according to some embodiments of the present disclosure, is illustrated. In some embodiments, the needle 510 may include a bevel 515, a lumen 520, and a female locking mechanism 525. In some aspects, the bevel 515 may include an angled, sharpened tip of the needle, wherein the bevel 515 may be configured to penetrate bodily tissue smoothly and with minimal discomfort. By way of example and not limitation, the bevel 515 may be configured to penetrate the celiac plexus.

In some embodiments, the needle may include a lumen 520, wherein the lumen 520 may include the hollow cavity that runs the length of the needle. In some implementations, the female locking mechanism 525 may include a Huber lock. In some aspects, the female locking mechanism 525 may be configured to connect to a fluid containing portion of an injector device. In some aspects, the female locking mechanism 525 may include a hollow cavity that may be configured to transfer fluids from the fluid containing portion to through the lumen 520 and the bevel 515. By way of example and not limitation, the fluid may include anesthesia.

Figure 6:
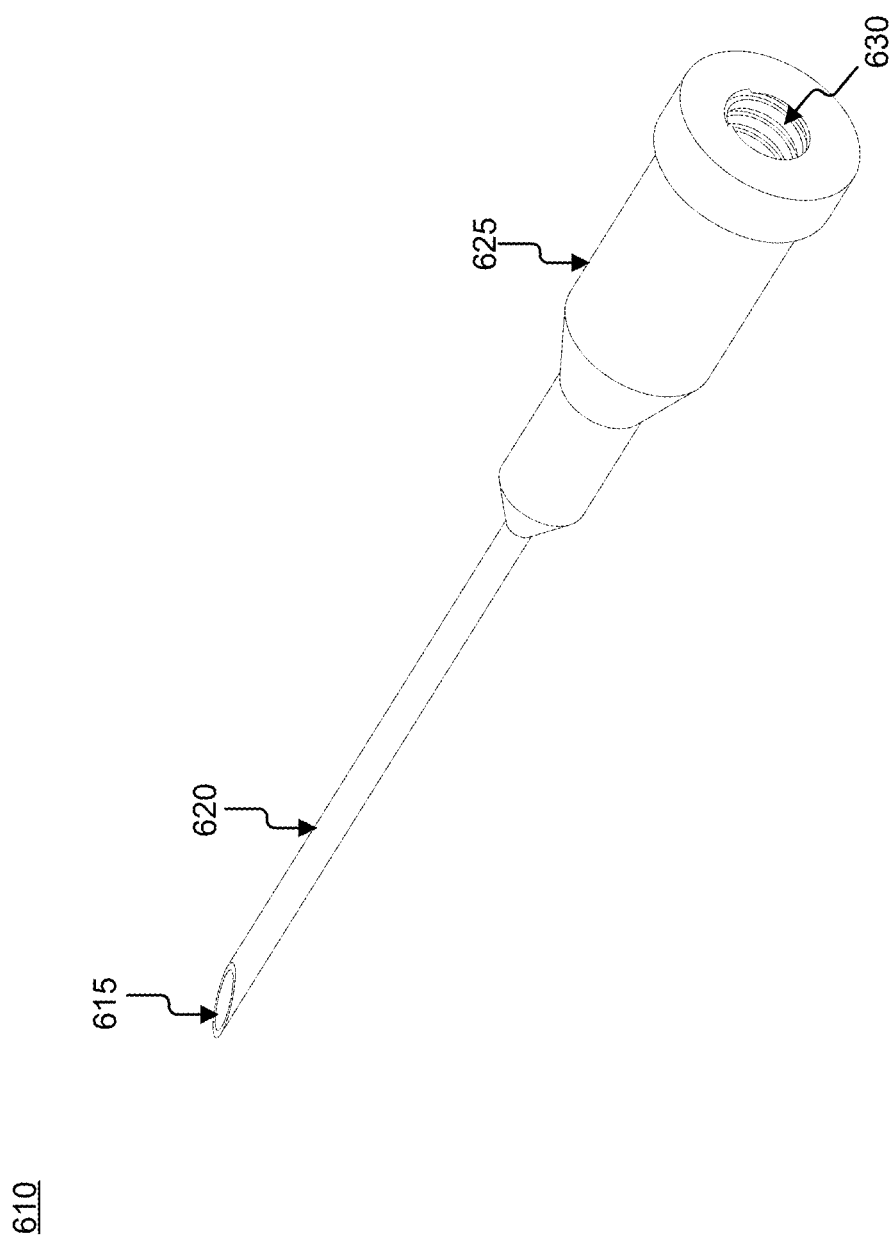
FIG. 6 illustrates a needle of an injector device, according to some embodiments of the present disclosure

Referring now to FIG. 6, a needle of an injector device, according to some embodiments of the present disclosure, is illustrated. In some embodiments, the needle 610 may include a bevel 615, a lumen 620, and a female locking mechanism 625. In some implementations, the female locking mechanism 625 may include a threaded interior 630, wherein the threaded interior 630 may be configured to receive the male locking mechanism of a canula. In some implementations, the male locking mechanism may include a threaded exterior configured to twist into the female locking mechanism 625, wherein the male locking mechanism and female locking mechanism 625 may securely connect the needle 610 to the canula. In some aspects, the female locking mechanism 625 may include a partially hollow interior, wherein fluid may flow through the female locking mechanism 625 through the lumen 620 and out of the bevel 615.

Figure 7:
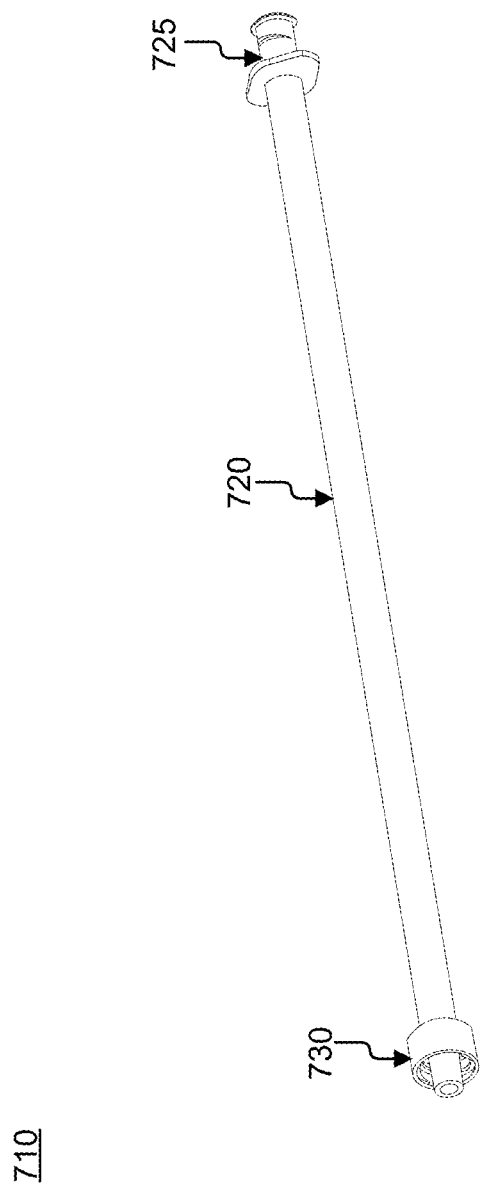
FIG. 7 illustrates a canula of an injector device, according to some embodiments of the present disclosure

Referring now to FIG. 7, a canula of an injector device, according to some embodiments of the present disclosure, is illustrated. In some embodiments, the canula 710 may include a rigid piping 720, a female locking mechanism 725, and a male locking mechanism 730. In some implementations, the rigid piping 720 may extend the length of the canula 710 from the female locking mechanism 725 to the male locking mechanism 730. In some aspects, the female locking mechanism 725 may be configured to connect the canula 710 to the fluid containing portion of an injector device. In some implementations, the male locking mechanism 730 may be configured to connect the canula 710 to a needle.

In some embodiments, the canula 710 may include a hollow interior. By way of example and not limitation, fluids may be configured to travel through the canula 710. In some aspects, the fluids may include anesthesia, as a non-limiting example. By way of example and not limitation, the canula 710 may be configured to provide additional reach to the injector device, wherein the canula 710 may be positioned in a port of a patient's body, wherein the canula 710 may provide length to allow the needle to a network of nerves. In some aspects, the canula 710 may be configured to provide the length necessary for the needle to reach the celiac plexus.

Figure 8:
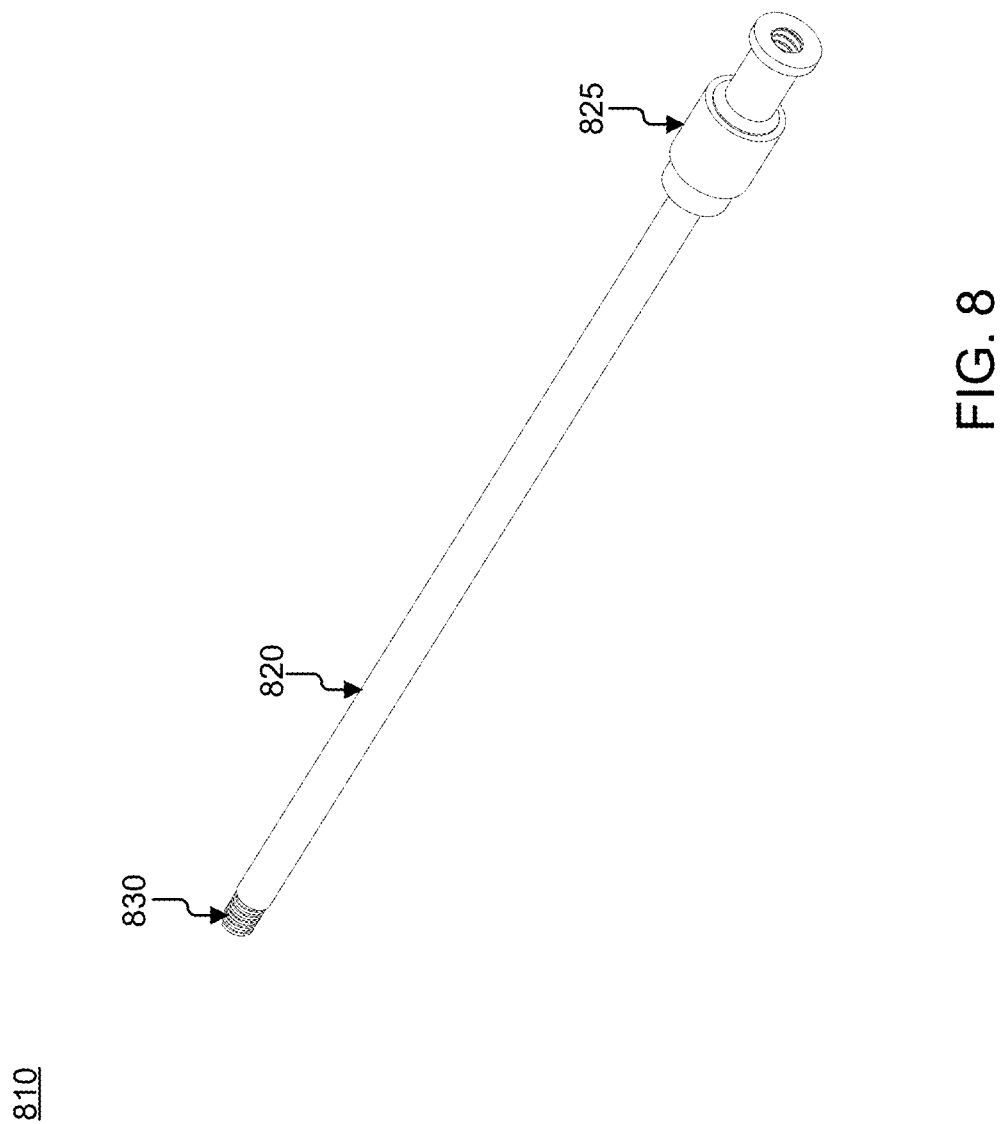
FIG. 8 illustrates a canula of an injector device, according to some embodiments of the present disclosure

Referring now to FIG. 8, a canula of an injector device, according to some embodiments of the present disclosure, is illustrated. In some embodiments, the canula 810 may include a rigid piping 820, a female locking mechanism 825, and a male locking mechanism 830. In some aspects, the female locking mechanism 825 may include a threaded interior configured to connect to a threaded exterior of the fluid containing portion. In some implementations, the male locking mechanism 830 may include a threaded exterior configured to connect with a threaded interior of a needle. In some aspects, the threaded exterior of the male locking mechanism 830 and the threaded interior of the female locking mechanism 825 may include a hollow interior that extends through the rigid piping 820, wherein fluid may travel across the canula 810 from the fluid containing portion to the needle.

Figure 9:
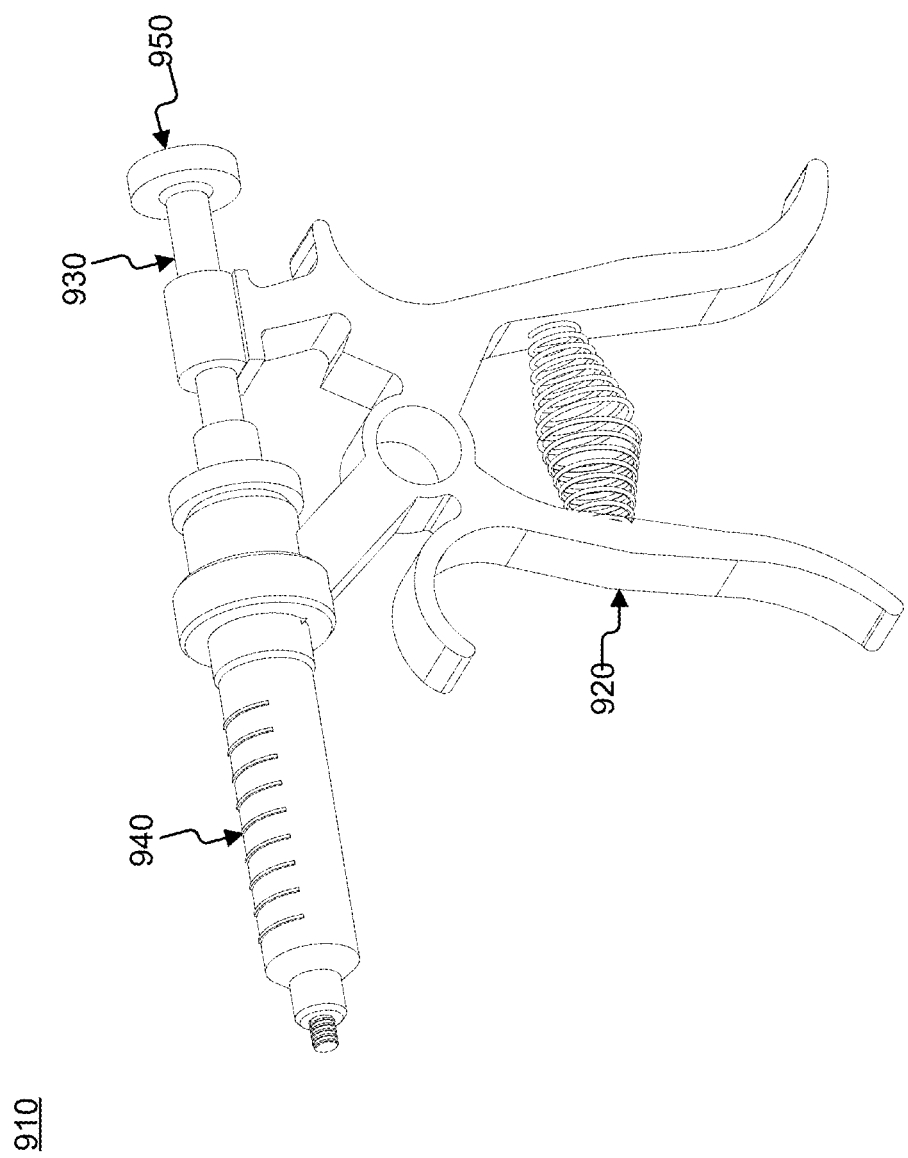
FIG. 9 illustrates an injector device, according to some embodiments of the present disclosure

Referring now to FIG. 9, an injector device, according to some embodiments of the present disclosure, is illustrated. In some embodiments, the injector device 910 may include an injector handle 920, a loading mechanism 930, and a fluid containing portion 940. In some implementations, the fluid containing portion 940 may be configured to contain fluid. In some aspects, the fluid may include anesthesia. In some aspects, the fluid containing portion 940 may include a male locking mechanism 945 configured to connect to the female locking mechanism of a canula.

In some embodiments, the loading mechanism 930 may be partially configured inside of the fluid containing portion 940, wherein the loading mechanism 930 may include a disc-like apparatus within the fluid containing portion 940. By way of example and not limitation, the disc-like apparatus may be configured to fit the width of the fluid containing portion 940, wherein the loading mechanism 930 creates a suction to withdraw and expel the fluid. In some aspects, the end of the loading mechanism 930 opposite of the fluid containing portion 940 may include a knob 950, wherein the knob 950 may be used both as leverage to push and pull the loading mechanism 930. In some aspects, the knob 950 may be configured to prevent the loading mechanism 930 from moving too far through the fluid containing portion 940.

In some embodiments, pulling the loading mechanism 930 may create a suction to draw fluids through a needle, through a canula, and into the fluid containing portion 940. In some aspects, the pushing of the loading mechanism 930 may force the fluids out of the fluid containing portion 940, through the canula, and through the needle in a controlled manner.

Figure 10:
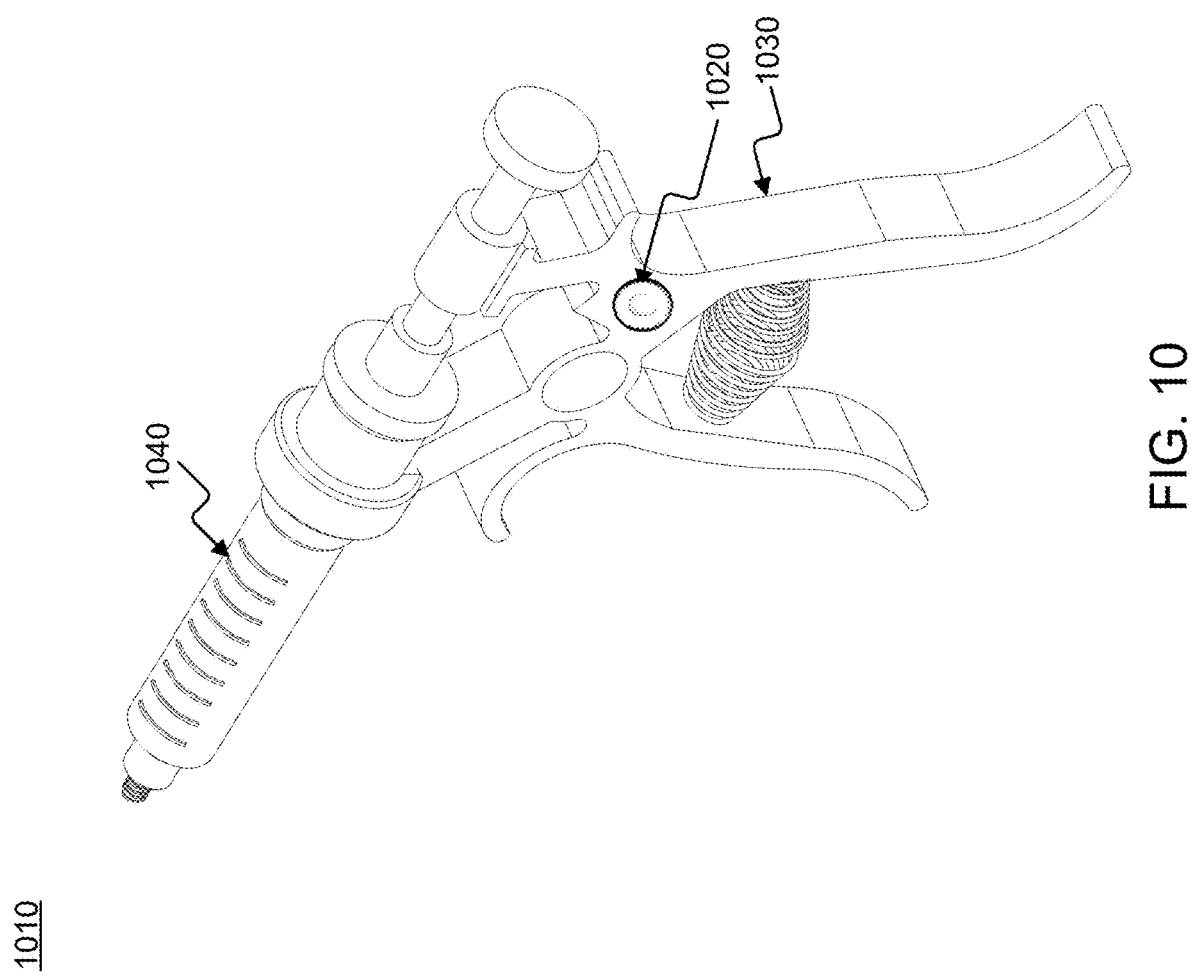
FIG. 10 illustrates an injector device, according to some embodiments of the present disclosure The Figures are not necessarily drawn to scale, as their dimensions can be varied considerably without departing from the scope of the present disclosure.

Referring now to FIG. 10, an injector device, according to some embodiments of the present disclosure, is illustrated. In some embodiments, the injector device 1010 may include an adjustment mechanism 1020, wherein the adjustment mechanism 1020 may be configured to determine the amount of fluid that may be expelled when pressure may be applied to an injector handle 1030. In some implementations, the adjustment mechanism 1020 may be mechanically coupled to the injector handle 1030, wherein the adjustment mechanism 1020 may include a lever, knob, or buttons, as non-limiting examples, wherein the adjustment mechanism 1020 may control the amount of fluid that may be expelled from the fluid containing portion 1040. In some embodiments, the adjustment mechanism 1020 may be set at a predetermined setting, wherein the predetermined setting may set an exact amount of fluid dispensed by the injector device 1010 when pressure may be applied to the injector handle 1030. By way of example and not limitation, the predetermined settings may correspond to the volume of fluid.

CONCLUSION

A number of embodiments of the present disclosure have been described. While this specification contains many specific implementation details, these should not be construed as limitations on the scope of any disclosures or of what may be claimed, but rather as descriptions of features specific to particular embodiments of the present disclosure.

Certain features that are described in this specification in the context of separate embodiments can also be implemented in combination or in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system components in the embodiments described above should not be understood as requiring such separation in all embodiments, and it should be understood that the described components and systems can generally be integrated together in a single product or packaged into multiple products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

Reference in this specification to "one embodiment," "an embodiment," any other phrase mentioning the word "embodiment", "aspect", or "implementation" means that a particular feature, structure, or characteristic described in connection with the embodiment is included in at least one embodiment of the disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional.

Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

What is claimed is:

1. An injector device configured to withdraw and deposit fluids including:
   a fluid containing portion including a fluid transfer end and a fluid control end distally located from the fluid transfer end, wherein the fluid containing portion is configured to contain a predefined amount of fluid, wherein fluid is received and ejected through the fluid transfer end, and wherein the fluid control end is configured to connect the fluid containing portion to a loading mechanism;
   an injector handle with a compression mechanism configured to create pressure between the injector handle, wherein applying pressure to the injector handle is configured to release a predefined amount of fluid contained in the fluid containing portion through the fluid transfer end;
   the loading mechanism detachably connected to the fluid control end and above the injector handle configured to slide within the fluid containing portion positioned adjacent to the loading mechanism, wherein the loading mechanism is configured to draw in a predefined amount of fluid into the fluid containing portion to control the amount of fluid inside the fluid containing portion, and wherein the loading mechanism includes a knob configured to provide leverage to push and pull the loading mechanism;
   a canula including rigid body with a first end and a second end distally located from the first end, wherein the rigid body includes a cylindrical extension, wherein the second end is detachably connected to the fluid dispensing end;
   a needle including an attaching end and an injecting end, wherein the attaching end is detachably connected to the first end of the canula;
   a first locking mechanism detachably connecting the fluid transfer end of the fluid containing portion to the second end of the canula;
   a second locking mechanism detachably connecting the first end of the canula to the attaching end of the needle, wherein the needle and the canula include an internal cavity connectable to the fluid containing portion, wherein the fluids are configured to enter and exit at the needle.

2. The injector device of claim 1, wherein the loading mechanism is partially configured inside of the fluid containing portion, wherein the loading mechanism includes a disc-like apparatus within the fluid containing portion that fits the width of the loading mechanism to create a suction to withdrawn and expel the fluid.

3. The injector device of claim 1, wherein the fluid is anesthesia or a numbing agent.

4. The injector device of claim 1, wherein the first locking mechanism and the second locking mechanism each include a female portion and a male portion, wherein the female portion is configured to receive the male portion.

5. The injector device of claim 4, wherein the attaching end of the needle includes the female portion configured to receive the male portion located on the first end of the canula.

6. The injector device of claim 4, wherein the first locking mechanism includes the canula with a female portion configured to receive the male portion from the fluid containing portion, wherein the connection between the male portion of the fluid containing portion and the female portion of the needle provides a secure connection.

7. The injector device of claim 1, further including an adjustment mechanism on the injector device that is mechanically coupled to the injector handle and the fluid containing portion, wherein the adjustment mechanism sets a predetermined amount of the fluid that is expelled from the fluid containing portion when pressure is applied to the injector handle.

8. The injector device of claim 7, wherein the adjustment mechanism includes predetermined settings that are selected by the user, wherein each of the predetermined settings corresponds to a volume of fluid.

9. The injector device of claim 1, wherein the second locking mechanism is a Luer lock.

10. The injector device of claim 1, wherein the canula is configured to provide additional reach to the injector device, wherein the canula is configured to be positioned at a port of a patient's body to provide length for the needle to reach its targeted position.

11. The injector device of claim 1, wherein the compression mechanism is a spring.

12. The injector device of claim 1, further including a stopping mechanism connected to loading mechanism, wherein the stopping mechanism is below the loading mechanism and is configured to prevent the loading mechanism from moving.

13. A method for injecting fluids including:
  inflating a portion of the body with air through pneumoperitoneum, wherein the portion of the body is subject to a surgical procedure;
  setting a predefined amount of anesthesia deployable by an injector device, wherein the injector device includes:
    a fluid containing portion including a fluid transfer end and a fluid control end distally located from the fluid transfer end, wherein the fluid containing portion is configured to contain a predefined amount of fluid, wherein fluid is received and ejected through the fluid transfer end, and wherein the fluid control end is configured to connect the fluid containing portion to a loading mechanism;
    an injector handle with a compression mechanism configured to create pressure between the injector handle, wherein applying pressure to the injector handle is configured to release a predefined amount of fluid contained in the fluid containing portion through the fluid transfer end;
    the loading mechanism detachably connected to the fluid control end and above the injector handle configured to slide within the fluid containing portion positioned adjacent to the loading mechanism, wherein the loading mechanism is configured to draw in a predefined amount of fluid into the fluid containing portion to control the amount of fluid inside the fluid containing portion;
    a canula including rigid body with a first end and a second end distally located from the first end, wherein the rigid body includes a cylindrical extension, wherein the second end is detachably connected to the fluid dispensing end;
    a needle including an attaching end and an injecting end, wherein the attaching end is detachably connected to the first end of the canula;
    a first locking mechanism detachably connecting the fluid transfer end of the fluid containing portion to the second end of the canula;
    a second locking mechanism detachably connecting the first end of the canula to the attaching end of the needle, wherein the needle and the canula include an internal cavity connectable to the fluid containing portion, wherein the fluids are configured to enter and exit at the needle;
  maneuvering the injector device through a port located at the pneumoperitoneum;
  piercing a network of nerves with the needle of the injector device; and
  applying pressure to the injector handle to deliver predefined amount of anesthesia to the network of nerves.

14. The method of claim 13, wherein the surgical procedure is laparoscopic surgery.

15. The method of claim 14, wherein the network of nerves is the celiac plexus, wherein the application of anesthesia reduces abdominal pain following laparoscopic surgery.

16. The method of claim 14, wherein the port includes a disc-like entryway, wherein the port is a rigid structure with a circular aperture that is placed on an opening of a patient's body to keep it open and visible.

17. The method of claim 13, wherein the port is placed on the body to provide direct access to deep tissue or internal organs.

* * * * *